Jan. 7, 1958 F. MEILLAND Plant Pat. 1,672
ROSE PLANT
Filed April 29, 1957
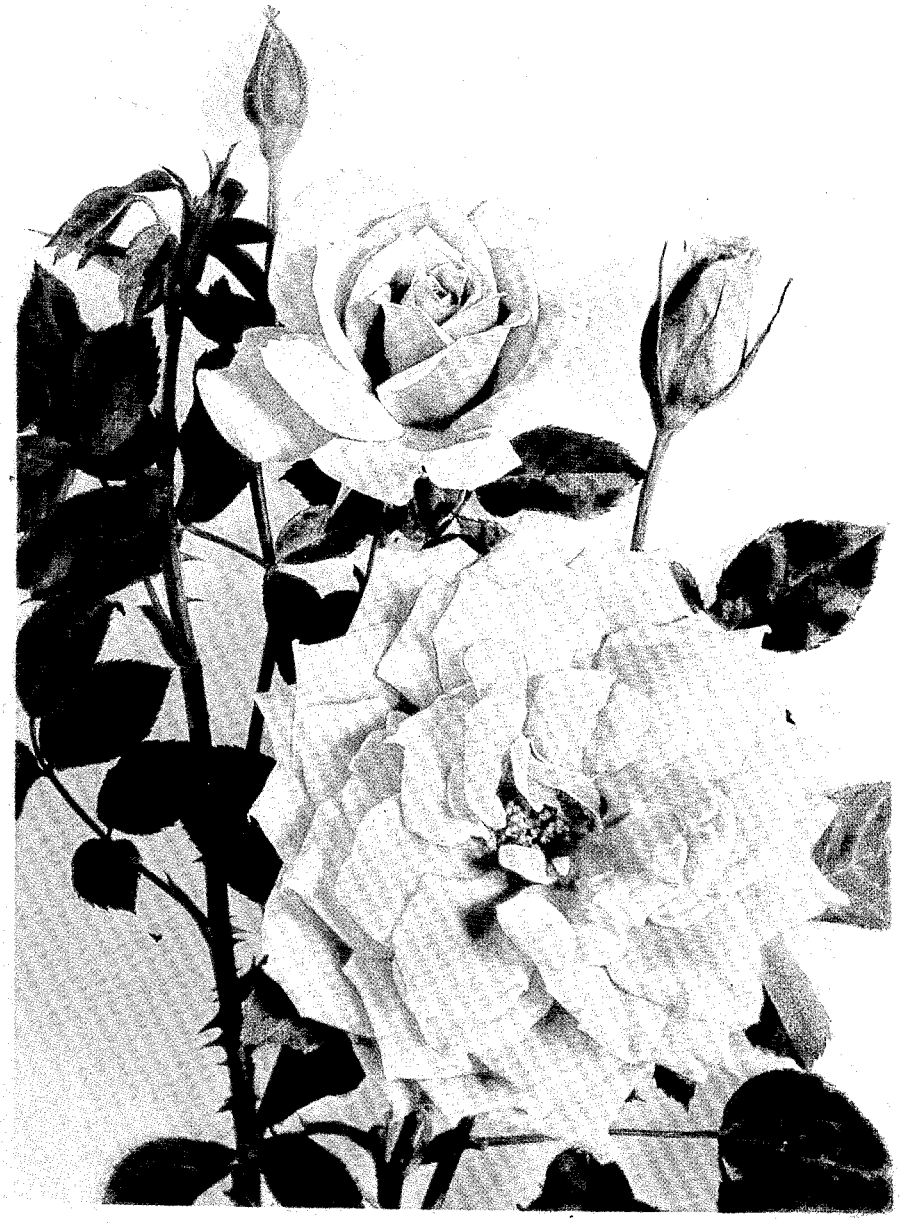
Inventor.
Francis Meilland
By: Robb & Robb
Attorneys.

United States Patent Office

Plant Pat. 1,672
Patented Jan. 7, 1958

1,672

ROSE PLANT

Francis Meilland, Cap Azura, Cap d'Antibes, France, assignor to The Conard-Pyle Company, West Grove, Pa., a corporation of Pennsylvania Application April 29, 1957, Serial No. 655,930

1 Claim. (Cl. 47—61)

The present invention relates to a new and distinct variety of rose plant of the hybrid polyantha class, which was originated by me by crossing the variety "Fantastique" (U. S. Plant Patent No. 574) with an unnamed and unpatented seedling derived from a cross of "Ampere" (unpatented × ("Chas. P. Kilham" × "Capucine Chambard") (all unpatented).

The primary objective of this breeding was to produce a new and improved Lavender Purple rose which combines therein the most desirable characteristics of its parents. This objective was fully achieved, as evidenced by the following unique combination of characteristics which are not found together in either parent or in any other variety of which I am aware:

(1) A compact habit of growth;

(2) The perfect form of the very double blooms;

(3) The good substance and long-lasting qualities of the flower petals; and (4) The unique Roseine Purple general color tonality of the blooms which is well maintained throughout their life.

Asexual reproduction of my new variety by budding, as performed by me in France, and as performed on my behalf at West Grove, Pennsylvania, U. S. A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Colour Chart of the Royal Horticultural Society, except where general color terms of ordinary dictionary significance are obvious:

Type: Hardy; bush; outdoor; seedling; for cut flowers and for garden decoration.

Class: Hybrid polyantha (floribunda).

Breeding: Seedling.

*Seed parent.*—"Fantastique."

*Pollen parent.*—An unnamed seedling of "Ampere" × ("Chas. P. Kilham" × "Capucine Chambard").

Propagation: Holds its distinguishing characteristics through succeeding propagations by budding.

*Flower*

Locality where grown and observed: West Groove, Pennsylvania, U. S. A.

Flowers borne: Several to stem; in regular, rounded clusters; on stems of medium length and normal strength.

Quantity of bloom: Abundant, outdoors.

Continuity: Continuous.

Fragrance: From slight to moderate. Nature—spicy.

Bud:

*Peduncle.*—Medium length; medium caliper; erect; almost smooth; with medium number of green hairs. Color—green.

*Before calyx breaks.*—Size—medium. Form—medium length; ovoid; with a conspicuous neck; with foliaceous appendages on the surface of the bud; with slender, little-cut foliaceous parts extending beyond the tip of the bud equal to ¼ or more of its length.

*As calyx breaks.*—Color—varying from Ruby Red, Plate 827, to Erythrite Red, Plate 0027, occasionally touched with China Rose, Plate 024/1.

*As first petal opens.*—Size—medium. Form—ovoid. Color: outside—Magenta Rose, Plate 027/1; inside—Rhodamine Purple, Plate 29/2, veined Fuchsia Purple, Plate 28/2.

*Opening.*—Opens up well.

Bloom:

*Size (when fully open).*—Medium; from 3 to 3½ inches.

*Petalage.*—Very double; from 35 to 42 petals; arranged regularly.

*Form.*—Cupped at first, and remaining cupped; petals at first being loosely rolled outward, but becoming tightly rolled outward later at maturity.

Petals:

*Texture.*—Leathery.

*Appearance.*—Inside—velvety. Outside—satiny.

*Shape.*—Outer petals—round, with one or two notches. Intermediate petals—round, with one notch and a point at apex. Inner petals—round, usually with one notch, but sometimes none.

This description of a newly opened flower was made from a rose that was grown outdoors in the month of July at West Grove, Pennsylvania, U. S. A.:

*Color.*—Outer petal: outside surface — Magenta, Plate 27/2, with point of attachment Sap Green, Plate 62; inside surface—Roseine Purple, Plate 629/2, with point of attachment Uranium Green, Plate 63/1. Intermediate petal: outside surface—Magenta, Plate 27/2, with point of attachment Sap Green, Plate 62; inside surface—Roseine Purple, Plate 629/2, with point of attachment Uranium Green, Plate 63/1. Inner petal: outside surface—Rhodamine Purple, Plate 29/2, occasionally streaked with Chartreuse Green, Plate 663/2, towards base of petal; inside surface—Roseine Purple, Plate 629/2, with point of attachment Uranium Green, Plate 63/2.

This description was made from a rose that was open for three days outdoors in the month of July, at West Grove, Pennsylvania, U. S. A.:

*Color.*—Outer petal: outside surface — Magenta Rose, Plate 027/3, with point of attachment Sap Green, Plate 62/1; inside surface—Orchid Purple, Plate 31/3, with point of attachment Uranium Green, Plate 63/2. Inner petal: outside surface—Rhodamine Purple, Plate 29/3, tinted with Rhodamine Purple, Plate 29/2, and usually with streaks of Chartreuse Green, Plate 663/2, towards base of petal; inside surface—Between Roseine Purple, Plate 629/2, and Roseine Purple, Plate 629/3, with base of petal Uranium Green, Plate 63/2.

*General color effect.*—Newly opened flower—Roseine Purple, Plate 629/2. Three days open—Orchid Purple, Plate 31/3 on outer petals, with inner petals showing Roseine Purple, Plate 629/2.

*Behaviour.*—Drop off cleanly.

*Flower longevity.*—On bush in garden—4 days in

July. Cut roses grown outdoors and kept at living room temperatures—3 days in July.

*Reproductive organs*

Stamens: Many; arranged regularly about pistils.
Filaments: Many; most with anthers; medium length. Color—Lemon Yellow, Plate 4/1.
Anthers: All open at once; medium size; seldom an anther fused with a petaloid. Color—Lemon Yellow, Plate 4.
Pollen: Moderate quantity. Color—Buttercup Yellow, Plate 5.
Pistils: Medium number.
Styles: Uneven; medium length; medium caliper; bunched.
Stigma: Color—Primrose, Plate 601/3.
Ovaries: All enclosed in receptacle.
Hips: None.
Sepals: Permanent; moderately long; spear-shaped.
Seeds: None.

*Plant*

Foliage:

Leaves.—Compound of 3 or 5 leaflets; normal abundance; medium size; leathery.

*Leaflets.* — Shape — oval. *Apex* — arcuminate. Base—arcute. Margin—simply serrate.

*Color.*—Mature: upper surface — Spinach Green, Plate 0960; under surface—Spinach Green, Plate 0960/3. Young: upper surface—Oxblood Red, Plate 00823/3, overlying various tones of green; under surface—near Oxblood Red, Plate 00823/3.

*Rachis* (*the supporting stem of the compound leaf*).—Medium caliper. Upper side—grooved; hairy. Under side—sparsely prickly.

*Stipules.*—Moderately long; narrow; with points of medium length turning out at an angle of more than 45°.

*Disease resistance.*—Comparable to that of the average variety, as determined from comparison with other varieties grown under the same cultural conditions at West Grove, Pennsylvania, U. S. A.

Growth:

*Habit.*—Bushy; much-branched.

*Growth.*—Vigorous.

*Canes.*—Medium caliper.

*Main stems.*—Color—Scheele's Green, Plate 860/1. Thorns—several; medium length; hooked or pointed downward; with medium, oval base. Prickles—none. Hairs—none.

*Branches.*—Color—Scheele's Green, Plate 860/2. Thorns—several; medium length; hooked or pointed downward; with medium, oval base. Prickles—none. Hairs—none.

*New shoots.*—Color—red. Thorns—several; medium length; straight; with medium oval base. Prickles—few; color—reddish. Hairs—none.

I claim:

A new and distinct variety of rose plant of the hybrid polyantha class, substantially as herein shown and described, characterized particularly as to novelty by its compact habit of growth, the perfect form of its very double blooms, the good substance and long-lasting qualities of the flower petals, and the Roseine Purple general color tonality of its blooms which is well-maintained throughout their life.

No references cited.